United States Patent [19]

Ludwig

[11] Patent Number: 5,298,130

[45] Date of Patent: Mar. 29, 1994

[54] METHOD OF MONITORING MAJOR CONSTITUENTS IN PLATING BATHS CONTAINING CODEPOSITING CONSTITUENTS

[75] Inventor: Frank A. Ludwig, Rancho Palos Verdes, Calif.

[73] Assignee: Hughes Aircraft Company, Los Angeles, Calif.

[21] Appl. No.: 976,117

[22] Filed: Nov. 13, 1992

[51] Int. Cl.$^5$ ............................................. G01N 27/26
[52] U.S. Cl. ................................. 204/153.1; 204/412; 204/434
[58] Field of Search ...................... 204/412, 434, 153.1, 204/DIG. 8, DIG. 9; 205/81, 101, 102, 103, 104, 105

[56] References Cited

PUBLICATIONS

Tench, Cyclic Pulse Voltammetric Stripping Analysis of Acid Copper Plating Baths, Apr. 1985, pp. 831–834.

*Primary Examiner*—John Niebling
*Assistant Examiner*—Bruce F. Bell
*Attorney, Agent, or Firm*—M. E. Lachman; M. W. Sales; W. K. Denson-Low

[57] ABSTRACT

A method of monitoring the concentration of metal ions comprising a major constituent in a plating bath which is insensitive to the effects of other codepositing constituents within the bath. The method involves applying a brief plating signal to a pretreated electrode positioned within the plating bath solution, applying a stripping signal to the plated electrode, and monitoring the resultant stripping signal response current. Certain characteristics of the stripping signal response current accurately indicate major constituent concentration levels and are unaffected by the codepositing constituents. The method complements and is easily integrated with known voltammetric techniques for analysis of trace constituents, thus forming an integral part of an efficient overall plating bath analysis system. By adjusting major constituent concentration levels in accordance with measurements made using the method of the present invention, a high quality plating bath can be easily and inexpensively maintained.

11 Claims, 1 Drawing Sheet

METHOD OF MONITORING MAJOR CONSTITUENTS IN PLATING BATHS CONTAINING CODEPOSITING CONSTITUENTS

This invention was made with support provided by the U.S. Government under Contract Number DAAB07-88-C-A047 awarded by the Department of the Army. The U.S. Government has certain rights to this invention.

BACKGROUND OF THE INVENTION

1. Field of the Invention

The present invention relates generally to plating baths and methods for monitoring the major constituents contained therein. More particularly, the method of the present invention relates to a voltammetric analysis technique that accurately indicates concentrations of metal ions comprising a major constituent within a plating bath containing additional codepositing constituents which would otherwise interfere with voltammetric measurement accuracy. The method can be used to maintain desired major constituent concentrations in order to ensure optimal plating bath performance.

2. Description of Related Art

A typical plating bath solution is comprised of a combination of several different electrochemical constituents. The specific constituents vary depending upon the type of plating bath, but in general can be broadly divided into what are commonly known as major constituents and trace, or minor, constituents. The major constituents are those electrochemical constituents which make up about 2 to 50 percent of the total bath weight or volume. Trace constituents, on the other hand, are present in smaller quantities, usually less than 1 percent of the total weight or volume. For example, in an acid cadmium plating bath, cadmium ions are a major constituent, and typically represent about 3 to 5 percent of the total bath weight. The acid cadmium plating bath might also contain trace constituents such as organic addition agents, degradation products and chemical contaminants, present in much smaller concentrations.

The concentration levels of both major and trace constituents are important determinants of the quality of the resultant plating deposit. Trace constituent concentrations influence certain characteristics of the plating deposit, including tensile strength, ductility, solderability, uniformity, brightness and resistance to thermal shock. Monitoring and optimization of trace constituents assumes that the major constituent concentrations within the bath are already properly set and maintained. Should the major constituents fall outside of required concentration ranges, however, the bath may fail to satisfactorily perform its plating function. It is therefore important that major constituent concentrations be regularly monitored.

Current techniques for monitoring the major constituents of plating baths typically involve removing a sample of the electrochemical solution from the plating tank for subsequent wet chemical analysis. Methods of measuring major constituent content in various types of plating baths are disclosed in K. E. Langford and J. E. Parker, "Analysis of Electroplating and Related Solutions," pages 83-100, 65-68 and 174-180. Wet chemical analysis methods such as these usually must be performed by highly skilled personnel. Specialized and costly chemical analysis equipment and supplies are required. Furthermore, the delay between drawing samples and receiving measurement results can be anywhere from several hours to several days. It is thus very tedious and expensive to monitor major constituent concentrations using currently available techniques. Moreover, the slow response time of wet chemical analysis limits the extent to which a high quality plating bath can be continuously maintained.

The current major constituent monitoring techniques are quite different from real time trace constituent monitoring techniques such as those in U.S. Pat. No. 4,631,116, assigned to the present assignee. The method disclosed therein uses voltammetric techniques to produce ac current spectra which vary as a result of changes in the concentration of various trace constituents. Voltammetric methods have been found to produce accurate results in real time for trace constituent analysis.

An important problem which may enter when voltammetric techniques are applied to major constituent analysis is that in many plating baths other trace or major constituents will codeposit on a sensing electrode with the major constituent being analyzed. For example, hydrogen ions coreduce and codeposit with metal ions to varying degrees in many types of acidic plating baths. Some voltammetric techniques rely upon a measurement of the total charge plated and then stripped from an electrode, usually in the form of a response current signal, to indicate the concentration of a desired constituent. When other constituents codeposit or are evolved with the desired constituent, the measured charge is influenced by these codepositing constituents. Coreduction and codeposition of other constituents such as hydrogen ions on a sensing electrode surface therefore reduces the accuracy of monitoring techniques such as dc voltammetric and anodic stripping, as well as ac techniques such as those disclosed in U.S. Pat. No. 4,631,116. Until this problem is resolved, voltammetric monitoring system accuracy will be insufficient for major constituent analysis of certain plating baths containing codepositing constituents.

In the case of the acid cadmium plating bath discussed above, hydrogen ions within the bath will codeposit with cadmium ions when a voltammetric signal is applied to a sensing electrode in contact with the bath. The charge due to the codepositing hydrogen will alter the resultant response current signal and prevent accurate measurement of cadmium ion concentration.

As a result of this problem, it is presently necessary to use voltammetric trace constituent measurement techniques in conjunction with other major constituent chemical analyses in order to accurately monitor the overall quality of a plating bath containing codepositing hydrogen. The wet chemical analysis cannot be performed with the in-tank electrochemical sensors and other equipment typically used in trace constituent analysis. Two different sets of equipment must therefore be maintained in order to perform major and trace constituent analysis. No integrated measurement system is available which is capable of measuring both major and trace constituents in plating baths containing codepositing constituents.

As is apparent from the above, there presently is a need for an accurate and inexpensive real time method of monitoring the concentration of major constituents within a plating bath containing other codepositing constituents such as hydrogen ions. Furthermore, the method should complement and be easily integrated with known techniques and equipment suitable for measuring trace constituents, resulting in an efficient overall plating bath analysis system.

SUMMARY OF THE INVENTION

In accordance with the present invention, a method for monitoring the concentration metal ions comprising a major constituent within a plating bath is disclosed. The present invention is based upon the discovery that by rapidly plating and stripping an additive-free electrode surface, and monitoring certain characteristics of the stripping response current signal, the concentration level of certain major constituents in the bath can be accurately determined despite the presence of other codepositing constituents. The method of the present invention thus makes possible the use of voltammetry to accurately determine major constituent concentrations in a wide variety of plating baths, including but not limited to those containing significant quantities of codepositing hydrogen ions.

The method of the present invention involves the steps of providing a sensing electrode in contact with a plating bath solution containing the metal ion major constituent; applying a pretreatment signal to the electrode in order to remove additives and contaminants from the electrode surface in preparation for subsequent plating and stripping; applying a plating signal to the pretreated electrode to plate a layer of metal onto the electrode surface; applying a stripping signal to the electrode to strip off the plating from the electrode; and monitoring signal characteristics of the stripping signal response current to determine particular major constituent concentrations.

In accordance with the present invention, one of the response current signal characteristics which may be monitored is the time required for this current to be reduced to zero. This time interval is not influenced by constituents which codeposit with the metal plating. By measuring the time required to strip the plating deposit from the electrode surface, rather than the total amount of charge stripped, the present invention accurately indicates major constituent concentration and is unaffected by codepositing constituents.

As a feature of the present invention, the method is highly selective and can accurately distinguish and monitor a desired major constituent in a plating bath containing codepositing constituents such as hydrogen ions. For example, the method will accurately determine cadmium ion concentration levels in an acid cadmium plating bath also containing a significant concentration of hydrogen ions. The method can also be used to monitor major constituent concentrations in other types of plating baths.

As another feature of the present invention, the method eliminates the delay, expense and complexity typically associated with current major constituent wet chemical analysis methods. Specialized chemical equipment and analysis personnel are no longer required. The measurement results are available in real time so that the ideal major constituent levels, and thereby the quality of the plating bath, can be continuously and efficiently maintained.

As a further feature of the present invention, the method is easily integrated with known trace constituent measurement methods and equipment, thereby providing an efficient and flexible overall plating bath analysis system suitable for accurately monitoring a wide variety of plating baths and their respective major constituents. Since the present invention can be implemented using voltammetric equipment suitable for trace constituents, only a single set of equipment need be maintained. The method of the present invention thus serves to complement and extend the capabilities of existing voltammetric analysis techniques.

As an additional feature of present invention, optimal signal parameters for monitoring the concentrations of an exemplary major constituent within a typical acid cadmium bath are disclosed. Furthermore, the method provides an experimental framework for determining optimal measurement signal parameters for monitoring major constituents in other types of plating baths.

The above-discussed features and attendant advantages of the present invention will become better understood by reference to the following detailed description of the invention and the accompanying drawings.

DESCRIPTION OF THE PREFERRED EMBODIMENTS

The present invention measures the concentration metal ions which are a major constituent in a plating bath solution in the presence of other codepositing constituents by rapidly plating and stripping a pretreated electrode. Monitoring the stripping signal response current provides an accurate and highly selective indication of the major constituent concentration level.

The present invention has wide application to many different plating baths and major constituents. Although the following description applies the method of the present invention to an exemplary acid cadmium bath containing cadmium ions as a major constituent along with varying quantities of codepositing hydrogen, it should be understood that this is by way of example and not limitation. The method of the present invention can selectively distinguish many other major constituents in the presence of a variety of codepositing constituents. Furthermore, although the present invention is particularly well-suited for measuring major constituent concentration in the presence of codepositing constituents, the method can also be used with plating baths in which codeposition does not occur.

Figure 1:
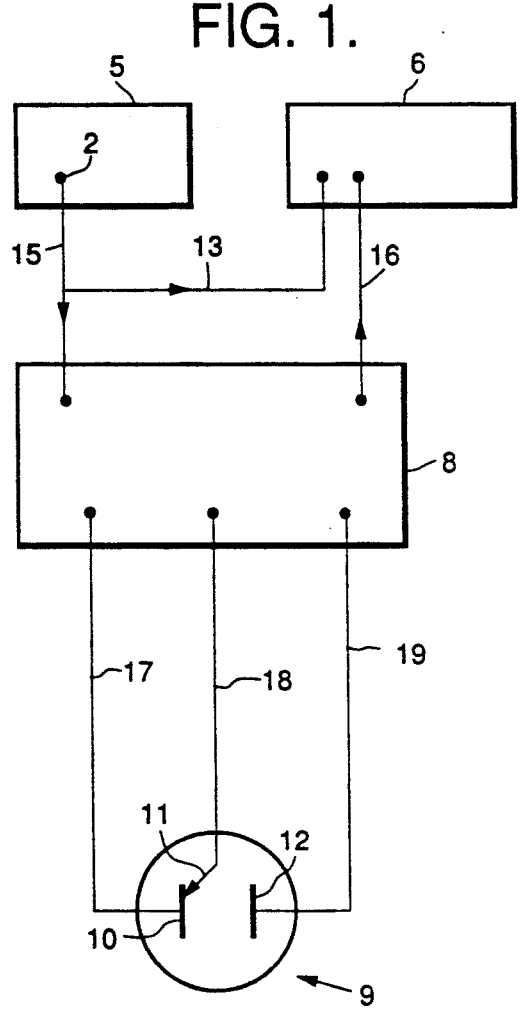
FIG. 1 is a schematic representation of a preferred exemplary system f or conducting the method in accordance with the present invention.

The schematic diagram of FIG. 1 illustrates a preferred exemplary system for conducting the method of the present invention. It should be noted that the equipment of this system is readily compatible with the equipment used in conjunction with voltammetric techniques used to monitor trace constituents. The present method therefore serves to extend the capability of these trace voltammetric techniques without the need for additional equipment.

Figure 2:
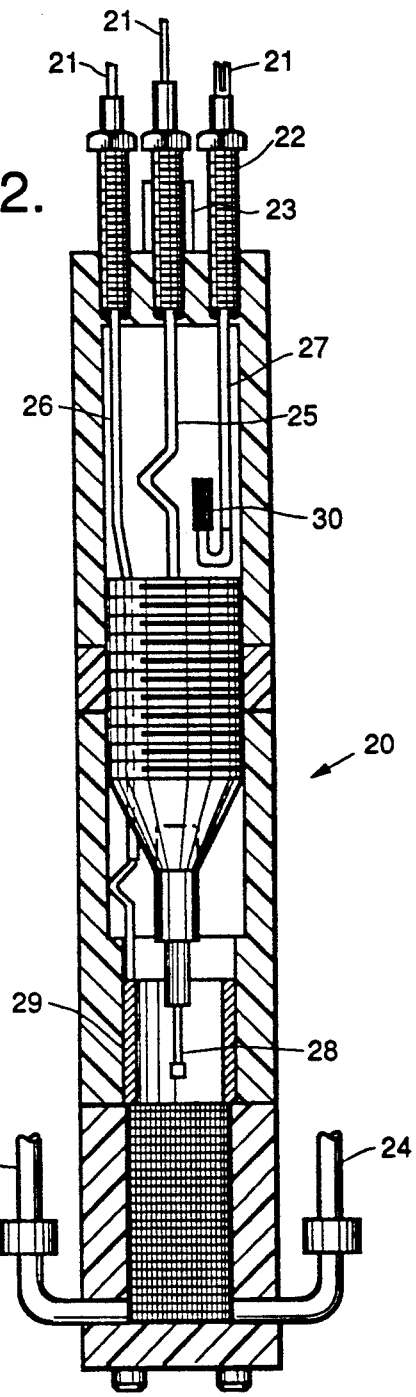
FIG. 2 is a detailed side sectional view of the exemplary electrochemical sensor which is shown schematically in FIG. 1.

In the exemplary system of FIG. 1, the plating bath solution is located within an electrochemical cell 9. The electrochemical cell 9 is preferably part of an electrochemical sensor submerged within the plating bath. One such exemplary in-tank sensor is shown in FIG. 2. The solution can be drawn into sensor 20 via inlets 24 by an external pump (not shown). The solution passes through the sensor 20 and back to the pump through outlet tube 23. Within the sensor 20, the solution is in contact with working electrode 28, counter electrode 29, and reference electrode 30. These electrodes are connected to the external wires 21 via leak-proof bushings 22 and insulated conductors 25, 26 and 27, respectively. The external wires 21 provide connections to the appropriate test equipment.

Referring again to the test equipment shown schematically in FIG. 1, the potentiostat 8 serves to generate an electrode pretreatment signal of appropriate amplitude and duration. The pretreatment signal removes any adsorbed organics or other contaminants from the electrode surface and otherwise prepares it for subsequent plating. Alternatively, the pretreatment signal could be supplied by the waveform generator 5.

The waveform generator 5 provides an output 15 which is an appropriate voltammetric signal waveform having a suitable amplitude and duration. The voltammetric signal is applied to the external input of potentiostat 8 and to the reference input of a display device 6. Alternatively, the voltammetric signal can be generated within the potentiostat itself. An exemplary potentiostat with internal signal generating capability is the PAR model 273 available from Princeton Applied Research, of Princeton, NJ. Display device 6 can include a digital data acquisition system, an oscilloscope or any other suitable display means. The potentiostat 8 further serves to ensure that the pretreatment and voltammetric signal remains constant despite variations in current flow through the electrochemical cell 9.

The pretreatment and voltammetric signals passing through or generated within potentiostat 8 are applied to the sensing electrode 10 in the electrochemical cell 9 via line 17. The electrochemical cell 9 also contains a counter-electrode 12 and a reference electrode 11. All system voltage measurements are taken relative to this reference electrode 11. The reference electrode can be a standard calomel reference or any other suitable reference electrode. The reference electrode 11 and counter electrode 12 are connected to the potentiostat 8 via lines 18, 19, respectively. This three-electrode electrochemical sensor design is suitable for use with many different voltammetric techniques.

When a voltammetric signal is applied to the pretreated sensing electrode 10, a response current is generated between the sensing electrode 10 and the counter electrode 12. The response current varies depending upon the electrochemical processes occurring at the surface of the sensing electrode 10. The electrochemical processes are a function of the major constituent concentrations, and the response current is therefore indicative of these concentrations. The response current passes back through the potentiostat 8 and is monitored on display device 6. From the potentiostat output the response current is applied to the signal input of display device 6 via line 16. A reference signal is supplied from the voltammetric signal source, either waveform generator 5 or potentiostat 8, to the reference input of the display device 6 as represented by line 13. The reference is coherent with the response current signal and permits accurate relative measurements using display device 6. The reference signal may serve only to trigger a time base in display device 6. The response current displays represent unique spectra which indicate the major constituent composition of the plating bath solution within the electrochemical cell.

In accordance with the present invention, the voltammetric equipment described above selectively determines major constituent concentrations in the following manner. The pretreatment signal is applied to the sensing electrode to remove contaminants and prepare the surface for subsequent plating. The voltammetric signal is then applied to the sensing electrode to ascertain the concentration level of a particular major constituent. The voltammetric signal consists of an appropriate plating signal waveform followed by an appropriate stripping signal waveform.

The method uses the variation in constituent adsorption and oxidation rates to measure concentration levels of particular major constituents in the presence of codepositing constituents. In the case of codepositing hydrogen, for example, a certain quantity of hydrogen ions will be adsorbed onto the electrode surface along with the metal ions during the very brief plating signal. However, the adsorbed hydrogen will not have sufficient time to evolve on the surface and affect deposition rates, since the stripping signal is applied immediately after the plating signal. The stripping signal quickly removes the adsorbed hydrogen from the electrode surface, and the duration of the response current will therefore reflect only the metal ion concentration. It has been found that the concentration of hydrogen ions in the plating bath affects the magnitude of the stripping current but not the stripping time. However, the concentration of metal ion affects the stripping time. The response current signal characteristics can then be readily correlated to major metal ion constituent concentration level.

In order to optimize the stripping signal response current signal accuracy as an indicator of major constituent concentration, it is necessary to vary a number of independent physical test parameters. These parameters include: (1) pretreatment signal amplitude and duration; (2) type of plating signal waveform; (3) plating signal amplitude and duration; (4) type of stripping signal waveform; (5) stripping signal amplitude and duration; and (6) stripping signal response current characteristic measured. These parameters were independently varied to determine the preferred system parameters for monitoring major constituents using the preferred voltammetric system of FIG. 1. It should be noted, however, that alternative combinations of pretreatment, plating and stripping signal parameters may also produce similar measurement results.

In general, certain system parameters are particularly well-suited for selectively monitoring particular major constituent concentrations in the presence of codepositing constituents. All potentials and voltages are given with respect to a saturated calomel electrode. The sensing electrode is preferably pretreated at an anodic potential of about +2.5 to +3.5 volts, for a period of about 5 to 15 seconds. Very brief dc pulse waveforms are preferred for the plating signals. A dc pulse signal, at a potential sufficiently cathodic to produce an average amplitude of about 100 to 1000 macm$^2$ for a duration of about 500 to 700 milliseconds (ms) is used as a plating signal, and a dc pulse voltage sufficiently anodic to strip the plated deposit over a duration of about 30 to 900 ms is used for the stripping signal. Alternatively, other rapid signal waveforms could be used.

It is important to choose the plating signal duration such that the adsorbed hydrogen or other codepositing constituent does not have sufficient time to evolve from the electrode surface. If the adsorbed codepositing constituent does evolve, it may influence the response current signal characteristics and measurement accuracy will be reduced. After the electrode surface has been properly plated, the response current produced by the stripping signal is monitored by determining the time interval between initial application of the stripping signal and the time at which the stripping signal response current is reduced to zero. By measuring the amount of time required to strip the plating, instead of the total charge stripped from the electrode, the method of the present invention is able to isolate the effect of the metal ions from that of the other codepositing constituents. The response current time interval can be readily correlated to concentration level of the desired major constituent despite the presence of codepositing constituents. Alternatively, other characteristics of the response current, such as the zero intercept of the maximum slope of decreasing stripping current, could be monitored.

The exemplary voltammetric system of FIG. 1 has been applied to the detection of cadmium ions in the acid cadmium plating bath discussed above which is available from Lea Ronal of Freeport, NY. The cadmium ions were a major constituent within this exemplary acid cadmium bath, at a concentration level of about 2 to 5 percent of total bath weight. The acid cadmium bath also contained codepositing hydrogen ions as sulfuric acid in a concentration of about 5 to 10 percent of total bath weight.

Figure 3:
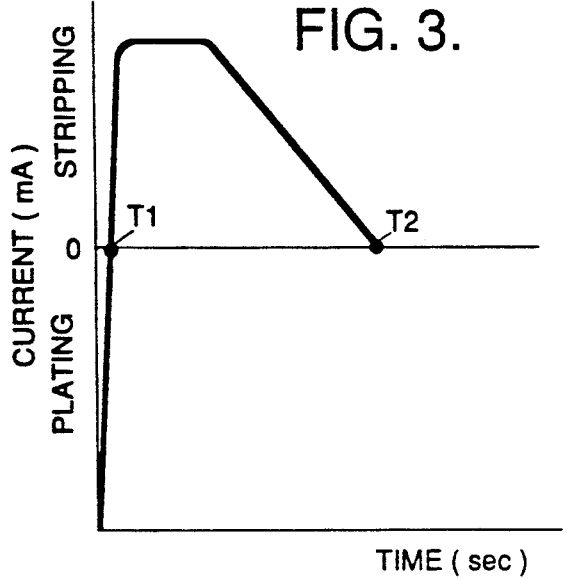
FIG. 3 is an illustration of an exemplary stripping signal response current produced at sensing electrode 28 in accordance with the present invention as applied to an acid cadmium plating bath containing cadmium and hydrogen ions. The duration of the response current indicates the cadmium ion concentration level.

The sensing electrode 10 in contact with the above-described exemplary solution was pretreated at an anodic potential of about +3.0 volts, for a period of about 10 seconds. A dc cathodic pulse waveform with an amplitude of about −2.0 volts and a duration of about 600 ms was used to plate the pretreated electrode. The duration of the plating signal was chosen such that the adsorbed hydrogen would not have sufficient time to evolve on the electrode surface. An anodic dc pulse signal with an amplitude of about +0.5 volts was then immediately applied to the plated electrode. The voltammetric stripping signal produced a response current which was monitored on display 6. An exemplary response current display is shown in FIG. 3. The time interval T2−T1 can be readily measured and is proportional to the concentration level of the cadmium ions. As discussed above, the adsorbed but non-evolved hydrogen ions did not affect the response current duration. Measurements are given in Table I.

TABLE I

| Stripping time at various cadmium and sulfuric acid concentrations | | |
|---|---|---|
| Cd ions (grams/liter) | Sulfuric acid (grams/liter) | Signal duration (ms) |
| 31.5 | 78.0 | 80, 82, 84 |
| 39.4 | 78.0 | 100, 102 |
| 39.4 | 93.6 | 101, 102 |
| 47.3 | 78.0 | 132, 132 |

Although the above example relates to a plating bath solution containing hydrogen ions as a codepositing constituent, this is by way of illustration and not limitation. The method can also be used to monitor other major constituents in the presence of other types of codepositing constituents. Furthermore, although the method is particularly well-suited to measurement of major constituents in the presence of codepositing constituents, the method can also be applied to plating baths in which no codepositing occurs. It will be understood by those skilled in the art that these and many other alternate implementations are possible without deviating from the scope of the invention, which is limited only by the appended claims.

What is claimed is:

1. A method of monitoring the concentration of metal ions comprising a major constituent present in a plating bath solution, said method comprising the steps of:
   providing at least one sensing electrode in contact with said solution;
   applying a pretreatment signal having an amplitude and duration to said sensing electrode in contact with said solution in order to remove contaminants from said sensing electrode to provide a substantially contaminant-free sensing electrode;
   applying a plating signal of an amplitude and duration to said contaminant-free sensing electrode, such that a portion of said metal ions from said solution form a plating on the surface of said sensing electrode to form a plated electrode wherein said plating signal is a dc pulse signal having potential which is cathodic to produce an average amplitude of about 100 to 1000 ma/cm$^2$ for a duration of about 500 to 700 ms;
   applying a stripping signal of an amplitude to said plated electrode, such that said plating on said surface of said plated electrode is removed, and further such that a stripping signal response current is produced, said stripping signal response current having signal characteristics indicative of the said major constituent concentration; and
   monitoring said signal characteristics of said stripping response current;
   wherein variations in said stripping response current signal characteristics provide an accurate indication of said major constituent concentration level.

2. The method of claim 1 wherein said metal ions comprise about 2 to 50 percent of the total weight of said plating bath solution.

3. The method of claim 1 wherein said plating bath solution further contains at least one additional constituent which will codeposit with said metal ions on said sensing electrode surface upon applying said plating signal.

4. The method of claim 3 wherein one of said additional constituents is hydrogen ions, said hydrogen being provided by sulfuric acid which comprises about 5 to 10 percent of the total weight of said plating bath solution.

5. The method of claim 1 wherein said pretreatment signal is an anodic dc signal with an amplitude of about 2.5 to 3.5 volts and a duration of about 5 to 15 seconds.

6. The method of claim 1 wherein said stripping signal is a dc pulse voltage which is anodic to strip the plated deposit over a duration of about 30 to 900 ms.

7. The method of claim 1 wherein said monitored signal characteristic of said stripping signal response current is the time interval between the initial application of said stripping signal to said electrode and the point at which said stripping signal response current is substantially reduced to zero, said time interval providing an accurate indication of said major constituent concentration.

8. The method of claim 4 wherein said plating bath is an acid cadmium plating bath and further wherein said monitored major constituent is cadmium ions.

9. The method of claim 8 wherein said pretreatment signal is a dc signal with an amplitude of about 2.5 to 3.5 volts and a duration of about 5 to 15 seconds.

10. The method of claim 8 wherein said plating signal has an amplitude of about 1.8 to 2.2 volts and a duration of about 500 to 700 ms.

11. The method of claim 8 wherein said anodic dc pulse stripping signal has an amplitude of about +0.3 to +0.7 volts.

* * * * *